(12) United States Patent
Condren

(10) Patent No.: US 6,278,021 B1
(45) Date of Patent: Aug. 21, 2001

(54) REDUCED PARTICLE-SIZE UREA

(76) Inventor: Sean Edward Paul Condren, 222 Queens Rd., Unit 63, Charlotte, NC (US) 28204

( * ) Notice: Subject to any disclaimer, the term of this patent is extended or adjusted under 35 U.S.C. 154(b) by 0 days.

(21) Appl. No.: 09/590,918

(22) Filed: Jun. 9, 2000

Related U.S. Application Data

(60) Provisional application No. 60/138,747, filed on Jun. 11, 1999.

(51) Int. Cl.[7] ........................ C07C 273/02; C07C 273/14
(52) U.S. Cl. .................................. 564/63; 521/82; 521/89; 521/90; 521/94; 521/99; 521/121; 521/128; 564/73
(58) Field of Search ........................ 564/63, 73; 521/82, 521/89, 90, 94, 99, 121, 128

(56) References Cited

U.S. PATENT DOCUMENTS

| | | | | |
|---|---|---|---|---|
| 3,625,887 | * | 12/1971 | Duecker et al. | 252/1 |
| 3,802,624 | * | 4/1974 | Kuhne et al. | 239/2 R |
| 4,954,154 | * | 9/1990 | Goertz | 71/3 |

* cited by examiner

*Primary Examiner*—Peter O'Sullivan
(74) *Attorney, Agent, or Firm*—Charles W. Calkins, Esq.; Kilpatrick Stockton LLP

(57) ABSTRACT

A process for producing an urea preparation of reduced particle-size and narrow particle-size distribution by using an air milling process is provided. Also provided is an urea preparation of reduced particle-size, narrow particle-size distribution, and high purity.

25 Claims, 7 Drawing Sheets

| PARAMETERS | | DISPERSER CONTROL | | % UNDER | SIZE | % UNDER | SIZE |
|---|---|---|---|---|---|---|---|
| Material | UREA | Disperser Type: | AeroDisperser | 5% | 5.38 | 55% | 17.20 |
| Density | 1.00 | Shear Force: | Med | 10% | 8.00 | 60% | 18.05 |
| Run Length (sec) | 219.8 | Feed rate: | Med | 15% | 9.60 | 65% | 18.88 |
| PMT Voltage (volts) | 1100.0 | Hyper Mode: | Off | 20% | 10.83 | 70% | 19.85 |
| Laser Intensity | 18 | Deagglomeration: | Normal | 25% | 11.86 | 75% | 20.91 |
| Clock Freq (MHz) | 40.0 | Pin Vibration | On | 30% | 12.83 | 80% | 22.19 |
| Sum of Channels | 170123 | Final feed | 100% | 35% | 13.72 | 85% | 23.49 |
| Lower Size Limit | 0.10 | Jet pressure: | 527.1 psi | 40% | 14.58 | 90% | 25.06 |
| Upper Size Limit | 220.00 | Pump pressure: | 21.1 psi | 45% | 15.44 | 95% | 26.52 |
| Nozzle Type | .200Mm | SCANS 98 AND | 99 COMBINED | 50% | 16.33 | | |
| Baseline Offset | 0.10 | BETWEEN 4.6 & | 6.6 MICRONS | | | | |
| Noise Filter | 6.00 | | | | | | |
| Mean Size | 14.98 | D(4,3): | 16.41 | Mode (Log Scale) | | 18.34 | |
| Standard Deviation | 1.65 | D(3,2): | 12.62 | Spec surf area: | | 0.475 sq meter/g | |

FIG. 3

| UPPER SIZE | % IN | LOWER SIZE | % UNDER | UPPER SIZE | % IN | LOWER SIZE | % UNDER | UPPER SIZE | % IN | LOWER SIZE | % UNDER | UPPER SIZE | % IN | LOWER SIZE | % UNDER |
|---|---|---|---|---|---|---|---|---|---|---|---|---|---|---|---|
| | | | | 100 | 0.00 | 86 | 100.00 | 10.0 | 4.86 | 8.6 | 11.65 | 1.00 | 0.02 | 0.86 | 0.01 |
| | | | | 86 | 0.00 | 74 | 100.00 | 8.6 | 3.11 | 7.4 | 8.54 | 0.86 | 0.01 | 0.74 | 0.00 |
| | | | | 74 | 0.00 | 63 | 100.00 | 7.4 | 2.11 | 6.3 | 6.43 | 0.74 | 0.00 | 0.63 | 0.00 |
| | | | | 63 | 0.00 | 54 | 100.00 | 6.3 | 1.40 | 5.4 | 5.03 | 0.63 | 0.00 | 0.54 | 0.00 |
| | | | | 54 | 0.00 | 46 | 100.00 | 5.4 | 1.33 | 4.6 | 3.07 | 0.54 | 0.00 | 0.46 | 0.00 |
| | | | | 46 | 0.00 | 40 | 100.00 | 4.6 | 0.94 | 4.0 | 2.76 | 0.46 | 0.00 | 0.40 | 0.00 |
| | | | | 40 | 0.00 | 34 | 100.00 | 4.0 | 0.85 | 3.4 | 1.91 | 0.40 | 0.00 | 0.34 | 0.00 |
| | | | | 34 | 0.00 | 29 | 89.75 | 3.4 | 0.60 | 2.9 | 1.31 | 0.34 | 0.00 | 0.29 | 0.00 |
| | | | | 29 | 10.25 | 25 | 79.34 | 2.9 | 0.39 | 2.5 | 0.92 | 0.29 | 0.00 | 0.25 | 0.00 |
| | | | | 25 | 10.41 | 22 | 59.68 | 2.5 | 0.26 | 2.2 | 0.67 | 0.25 | 0.00 | 0.22 | 0.00 |
| 220 | 0.00 | 180 | 100.00 | 22 | 19.66 | 18 | 48.25 | 2.2 | 0.29 | 1.8 | 0.38 | 0.22 | 0.00 | 0.18 | 0.00 |
| 180 | 0.00 | 160 | 100.00 | 18 | 11.43 | 16 | 36.67 | 1.8 | 0.12 | 1.6 | 0.25 | 0.18 | 0.00 | 0.16 | 0.00 |
| 160 | 0.00 | 140 | 100.00 | 16 | 11.57 | 14 | 24.68 | 1.6 | 0.11 | 1.4 | 0.15 | 0.16 | 0.00 | 0.14 | 0.00 |
| 140 | 0.00 | 120 | 100.00 | 14 | 11.00 | 12 | 16.51 | 1.4 | 0.08 | 1.2 | 0.07 | 0.14 | 0.00 | 0.12 | 0.00 |
| 120 | 0.00 | 100 | 100.00 | 12 | 9.16 | 10 | | 1.2 | 0.05 | 1.0 | 0.02 | 0.12 | 0.00 | 0.10 | 0.00 |

FIG. 4

| PARAMETERS | | DISPERSER CONTROL | | % UNDER | SIZE | % UNDER | SIZE |
|---|---|---|---|---|---|---|---|
| Material | UREA | Disperser Type: | AeroDisperser | 5% | 5.38 | 55% | 16.45 |
| Density | 1.00 | Shear Force: | Med | 10% | 7.46 | 60% | 17.33 |
| Run Length (sec) | 166.0 | Feed rate: | Med | 15% | 8.73 | 65% | 18.27 |
| PMT Voltage (volts) | 1100.0 | Hyper Mode: | Off | 20% | 9.91 | 70% | 19.19 |
| Laser Intensity | 19 | Deagglomeration: | Normal | 25% | 11.01 | 75% | 20.21 |
| Clock Freq (MHz) | 40.0 | Pin Vibration | On | 30% | 12.01 | 80% | 21.47 |
| Sum of Channels | 398828 | Final feed: | 34% | 35% | 12.95 | 85% | 22.78 |
| Lower Size Limit | 0.10 | Jet pressure: | 12.2 psi | 40% | 13.84 | 90% | 24.45 |
| Upper Size Limit | 220.00 | Pump pressure: | 12.0 psi | 45% | 14.74 | 95% | 26.26 |
| Nozzle Type | .200 Mm | SCANS 70 AND 71 COMBINED | | 50% | 15.57 | | |
| Baseline Offset | 0.10 | BETWEEN 9.1 & 10.6 MICRONS | | | | | |
| Noise Filter | 6.00 | | | | | | |
| Mean Size | 14.53 | D(4,3): | 15.85 | Mode (Log Scale) | | | 18.62 |
| Standard Deviation | 1.65 | D(3,2): | 12.68 | Spec surf area: | | 0.473 | sq meter/g |

FIG. 6

| UPPER SIZE | % IN | LOWER SIZE | % UNDER | | UPPER SIZE | % IN | LOWER SIZE | % UNDER | | UPPER SIZE | % N | LOWER SIZE | % UNDER |
|---|---|---|---|---|---|---|---|---|---|---|---|---|---|
| | | | | | 100 | 0.00 | 86 | 100.00 | | 1.00 | 0.00 | 0.86 | 0.00 |
| | | | | | 86 | 0.00 | 74 | 100.00 | | 0.86 | 0.00 | 0.74 | 0.00 |
| | | | | | 74 | 0.00 | 63 | 100.00 | | 0.74 | 0.00 | 0.63 | 0.00 |
| | | | | | 63 | 0.00 | 54 | 100.00 | | 0.63 | 0.00 | 0.54 | 0.00 |
| | | | | | 54 | 0.00 | 46 | 100.00 | | 0.54 | 0.00 | 0.46 | 0.00 |
| | | | | | 46 | 0.00 | 40 | 100.00 | | 0.46 | 0.00 | 0.40 | 0.00 |
| | | | | | 40 | 0.00 | 34 | 100.00 | | 0.40 | 0.00 | 0.34 | 0.00 |
| | | | | | 34 | 0.84 | 29 | 99.16 | | 0.34 | 0.00 | 0.29 | 0.00 |
| | | | | | 29 | 7.58 | 25 | 91.58 | | 0.29 | 0.00 | 0.25 | 0.00 |
| | | | | | 25 | 9.64 | 22 | 81.94 | | 0.25 | 0.00 | 0.22 | 0.00 |
| 220 | 0.00 | 180 | 100.00 | | 22 | 18.27 | 18 | 63.67 | | 0.22 | 0.00 | 0.18 | 0.00 |
| 180 | 0.00 | 160 | 100.00 | | 18 | 11.18 | 16 | 52.19 | | 0.18 | 0.00 | 0.16 | 0.00 |
| 160 | 0.00 | 140 | 100.00 | | 16 | 11.54 | 14 | 40.95 | | 0.16 | 0.00 | 0.14 | 0.00 |
| 140 | 0.00 | 120 | 100.00 | | 14 | 11.03 | 12 | 29.93 | | 0.14 | 0.00 | 0.12 | 0.00 |
| 120 | 0.00 | 100 | 100.00 | | 12 | 9.54 | 10 | 20.39 | | 0.12 | 0.00 | 0.10 | 0.00 |

| UPPER SIZE | % IN | LOWER SIZE | % UNDER |
|---|---|---|---|
| 10.0 | 5.91 | 8.6 | 14.48 |
| 8.6 | 4.69 | 7.4 | 9.78 |
| 7.4 | 3.49 | 6.3 | 6.29 |
| 6.3 | 2.33 | 5.4 | 3.97 |
| 5.4 | 1.60 | 4.6 | 2.37 |
| 4.6 | 0.92 | 4.0 | 1.44 |
| 4.0 | 0.67 | 3.4 | 0.78 |
| 3.4 | 0.36 | 2.9 | 0.41 |
| 2.9 | 0.18 | 2.5 | 0.23 |
| 2.5 | 0.09 | 2.2 | 0.14 |
| 2.2 | 0.07 | 1.8 | 0.07 |
| 1.8 | 0.02 | 1.6 | 0.05 |
| 1.6 | 0.02 | 1.4 | 0.03 |
| 1.4 | 0.01 | 1.2 | 0.02 |
| 1.2 | 0.01 | 1.0 | 0.01 |

FIG. 7

REDUCED PARTICLE-SIZE UREA

This application claims priority to copending U.S. provisional patent Application No. 60/138,747, filed Jun. 11, 1999.

FIELD OF THE INVENTION

The present invention relates to the production of reduced particle-size urea which may also have a narrow particle-size distribution and a high purity. Such urea preparations are useful, especially in the manufacture of rubber articles.

BACKGROUND

Urea (($NH_2$)$_2$CO) has many industrial uses. During the production of rubber and plastic articles, urea may be added as an activator of azodicarbonamide(AZO)-type blowing agents. The urea functions to lower the decomposition temperature of the AZO-type agents in sponge rubber to normal curing temperatures. It is believed that urea accomplishes this effect largely by enhancing the movement of free radicals in the compound during vulcanization. It is desirable for urea used in the production of rubber or plastic to be of a generally small particle-size, a high surface area, and to have an overall uniform particle-size distribution. Small, uniform particle-size is desirable to aid in achieving homogeneous dispersion when urea is incorporated into rubber compositions, especially in the production of foam or sponge rubber.

To obtain urea preparations for use in the manufacture of rubber, the urea, initially in the form of prills, is subjected to a mechanical grinding process. Grinding processes currently employed generally involve the use of a grinding apparatus with steel plates with teeth or pins which rotate at high speeds. This process for grinding urea produces urea preparations which are prone to agglomeration, resulting in hardened clumps and fused particles. These clumps and fused particles do not disperse sufficiently in sponge rubber compounds and ultimately contaminate the cured rubber articles.

The undesirable clumping of urea preparations is due to a number of factors. The current grinding process exposes the urea powder to atmospheric moisture and generates heat. These factors are believed to increase clumping of urea due to its hygroscopic nature. Current attempts to control moisture absorption involve adding desiccants to the urea at levels of approximately 2–4% by weight. This results, however, in an urea composition which produces more airborne particles (dust) during handling. This dust is considered a serious health hazard in rubber factories. Attempts to control dust currently involve treating the urea preparation with an oil spray (approximately 1–2% by weight). Thus, current attempts to control undesirable characteristics of urea preparations result in the addition of chemicals which reduce the purity of the urea powder by 3–6%, and impart a darker color to the urea. The coloring of the urea preparation is undesirable, as such preparations have a greater uncontrolled effect on colored rubber produced using urea.

It would be desirable to produce urea preparations of lower average particle-size and narrow particle-size distributions which do not require additives such as desiccants or dust-reducing oils. Accordingly, one object of the present invention is to provide an process for producing such urea preparations.

SUMMARY OF THE INVENTION

The present invention provides a process for producing an urea preparation of reduced particle-size and narrow particle-size distribution by using an air milling process. Another aspect of the present invention provides an urea preparation of reduced particle-size, narrow particle-size distribution, and high purity. As used herein, the term "particle size" refers to particle diameter.

The present invention, and preferred embodiments thereof are described in more detail below with reference to the appended figures.

BRIEF DESCRIPTION OF THE DRAWINGS

FIG. 3 is a tabular representation of process parameters for one embodiment of the process of the invention. Included are tabulated size characteristics including standard deviation for the size distribution, as well as the calculated value of the specific surface area.

FIG. 4 is a tabular representation of the particle size distribution as shown in the graph of FIG. 2.

FIGS. 5 through 7 show data as in FIGS. 2 through 4, respectively, for another Example (Run 2) according to the process of the invention.

DETAILED DESCRIPTION OF THE INVENTION

During the development of the present invention, it was recognized that a combination of heat and moisture during conventional grinding processes was largely responsible for undesirable clumping of urea powders. It was determined that grinding of urea at a temperature below 132° F. avoided clumping. Because control of temperature and moisture exposure was incompatible with conventional grinding means, an alternate process for grinding was sought. This search resulted in the present invention which uses high air pressure to pulverize prills of urea at temperatures below 132° F.

Figure 1:
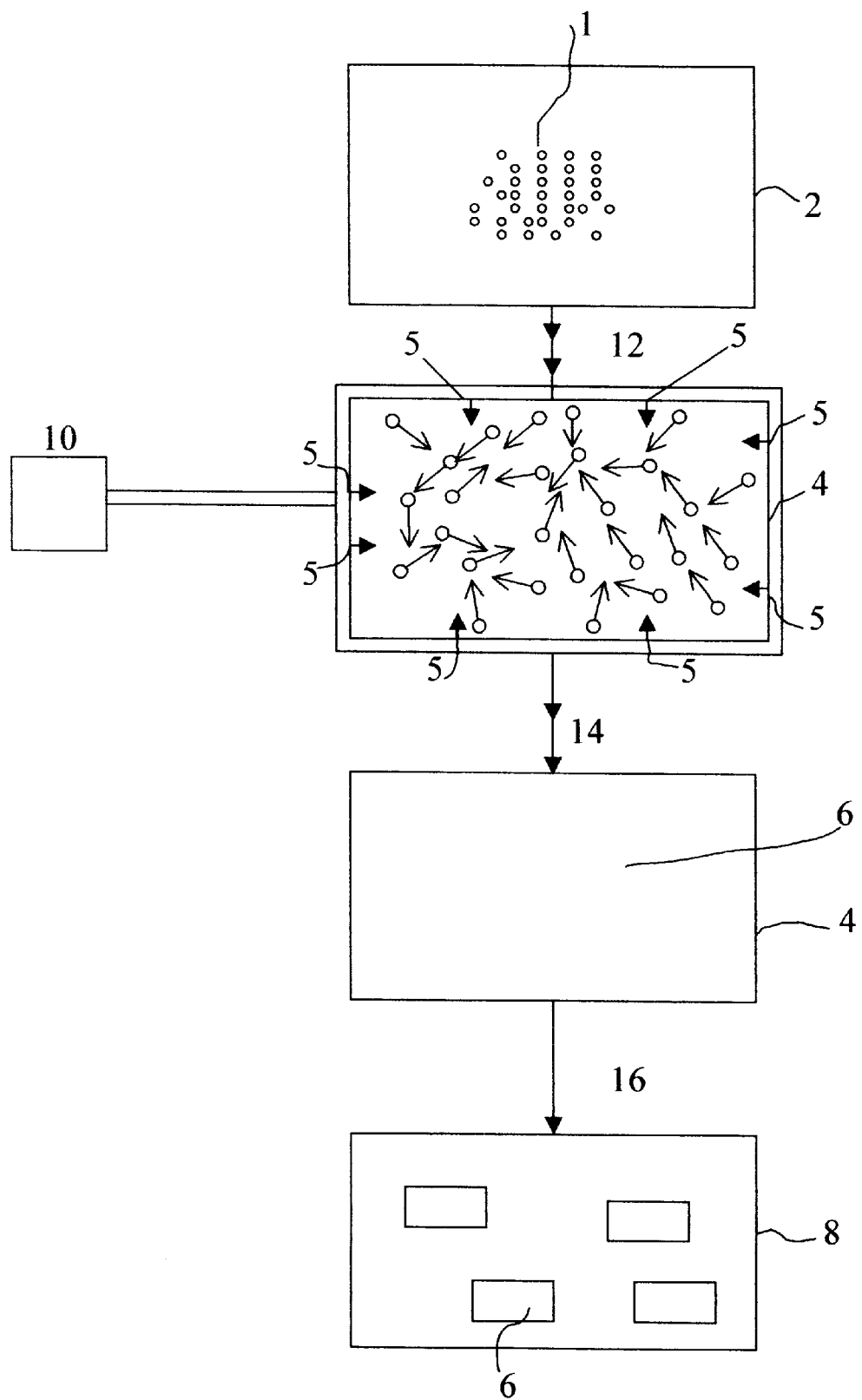
FIG. 1 is a diagrammatic depiction of an embodiment of the process of the present invention.

An embodiment of the process of the present invention is depicted diagrammatically in FIG. 1. As shown in FIG. 1, urea in the form of prills 1, is feed from a hopper 2 into the air mill chamber 4 at a predetermined flow rate 12. Inside the mill, the prills of urea 1 are subjected to blasts of air 5 from multiple angles. The force of the air blasts 5 causes the prills 1 to impact one another forcefully, so that the prills shatter. The self-impact process is controlled via the introduction of the air blasts 5 into the chamber of the air mill 4 using a precisely controlled source of high air pressure 10, such that the degree of size reduction of urea particles by impact with one another is consequently very controlled. The desired size reduction is achieved by controlling a combination of pressure and duration of the process. Once a desired level of size reduction of the urea particles 6 is achieved, the urea is removed 16 from the air mill and packaged 8.

The advantages of the process of the invention include the production of urea preparations with a small particle-size, a narrow particle size distribution, and a higher purity. The urea preparations according the present invention are of high purity, in part, because it is unnecessary to add desiccants to reduce clumping, and consequently unnecessary to add oils to reduce airborne dust (generally necessary when desiccants are added). The urea preparations of the invention are also whiter in appearance, and, consequently, have less affect on the color of rubber article produced using the preparations.

Air milling devices useful in the process of the present invention are commercially available, e.g. air classifier mills; and air jet mills. The process and preparations of the invention provide significant advantages. The urea preparations provided are particularly useful in rubber and plastic compounding. The urea preparation of the invention have reduced and uniform particle-size, thereby providing advantages, especially when used as activators for azodicarbonamide-type blowing agents in the production of sponge rubber. The characteristics of the ureas provided by the present invention may be generally desirable, however, in other applications where urea preparations are used.

Accordingly, in one aspect, the present invention relates to a process of producing urea preparations having a particle-size less than 50 $\mu$m using an air milling process. In a preferred embodiment, the mean particle-size is less than 40 $\mu$n. More preferably, the mean particle-size is less than 20 $\mu$m. Most preferably, the particle-size is about 15 $\mu$m.

In another preferred embodiment, the process results in an urea preparation having a particle-size distribution with a standard deviation of less than 1.7. More preferably, the standard deviation is about 1.55 to about 1.65. More preferably, the standard deviation is less than 1.65. Most preferably, the standard deviation is about 1.55.

In another preferred embodiment, the process results in an urea preparation having a purity of about 97% or greater. More preferably, the purity is about 98.5%.

In another aspect, the present invention relates to an urea preparation produced by the process of the invention.

In yet another aspect, the present invention relates to an urea preparation having a mean particle-size of less than about 50 $\mu$m. In a preferred embodiment, the mean particle size is less than about 40 $\mu$m. More preferably, the mean particle-size is less than about 20 pm. Most preferably, the mean particle-size is about 15 $\mu$m.

In another preferred embodiment, the urea preparation has a particle-size distribution with a standard deviation of about 1.55 to about 1.65. More preferably, the standard deviation is less than 1.65. Most preferably, the standard deviation is about 1.55.

In another aspect, the invention relates to an urea preparation having a particle-size of less than about 75 $\mu$m, a mean particle-size of less than about 40 $\mu$m, a particle-size distribution having a standard deviation of less than about 1.7, and a purity of greater than about 98.5%.

Table 1 presents general characteristics of a typical embodiment of the urea compositions of the invention ((NH$_2$)$_2$CO: Molecular weight=60.07; Specific gravity= 1.335).

| Item | Typical Properties | Test method |
| --- | --- | --- |
| Physical form | white powder | |
| Decomposition point | 271° F. | |
| Nitrogen weight | 46% min. | By difference |
| pH (10% solution @ 68° F.) | 7–10 | DCNA 10-U015 |
| Ash. ppm | 20 max. | DCNA 10-U009 |
| Alkalinity as ammonia, ppm | 150 max. | T.F.I. II. A.7 |
| Color, APHA | 10 max. | APHA 2120B |
| Sieve residue on 60 mesh* | 0% | L.O.P. 3.10 |
| Sieve residue on 100 mesh* | 0% - trace | L.O.P. 3.10 |

The urea compositions of the invention are useful as non-dusting, non-staining activators, e.g. with blowing agents and accelerators in rubber compounds. The compositions are useful in conjunction with blowing agents because it lowers the decomposition point of azodicarbonamide blowing agents to the curing temperature of rubber. The ureas of the invention also react with amine byproducts of azodicarbonamide blowing agents to reduce the amine odor. The compositions activate thiazole, thiuram, and dithiocarbamate accelerators, and are non-discoloring and non-staining.

EXAMPLES

Example 1

Figure 2:
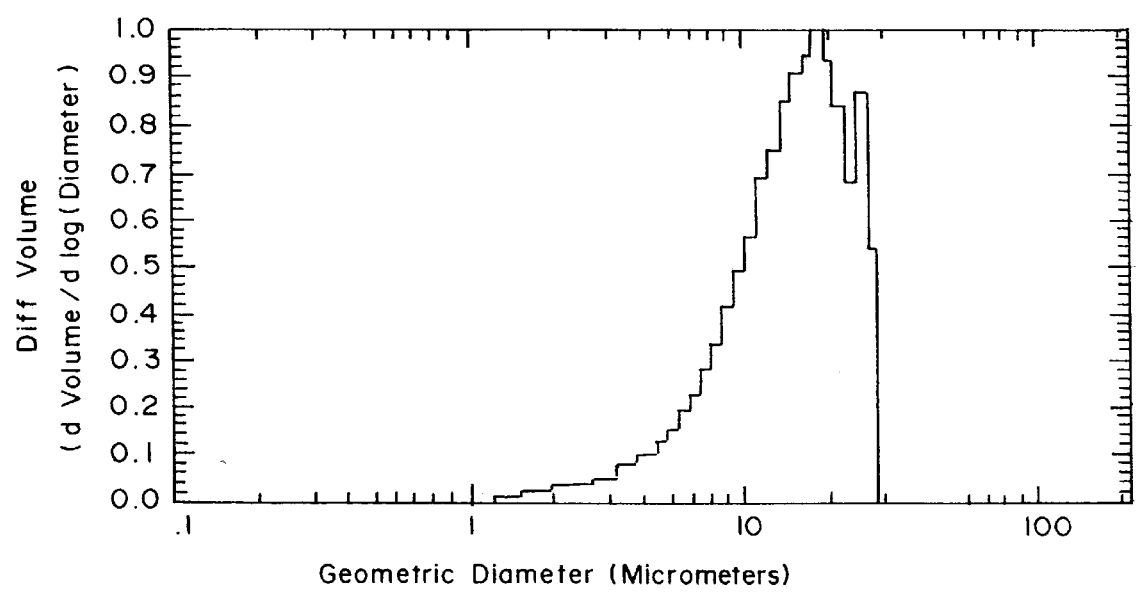
FIG. 2 is a graphic representation of the particle-size distribution of a process run of air milled urea (Example—Run 1) according to the process of the invention.

FIGS. 2–4 represent one example of an urea composition of the invention. Run 1, as indicated in the graphical depiction of FIG. 2, and in tabular form in FIGS. 3 and 4, is a composition with a mean size of 14.98 $\mu$m having a standard deviation of 1.65, and a specific surface area of 0.475 m$^2$/g.

Example 2

Figure 5:
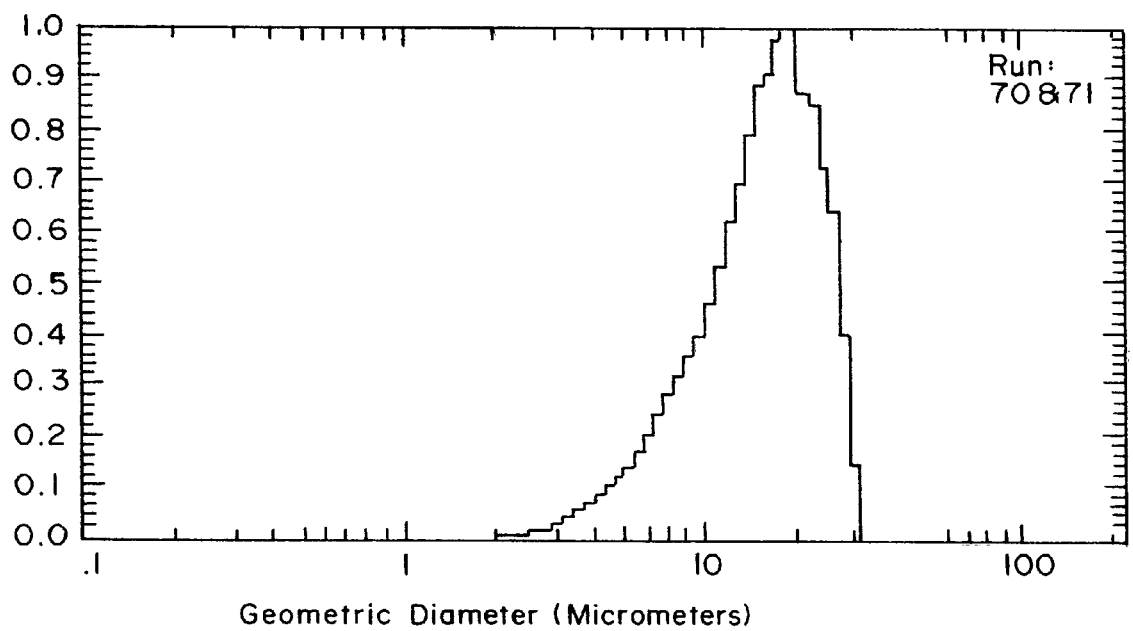

FIGS. 5–7 represent another example of an urea composition of the invention. Run 2, as indicated in the graphical depiction of FIG. 5, and in tabular form in FIGS. 6 and 7, is a composition with a mean size of 14.53 $\mu$m having a standard deviation of 1.60, and a specific surface area of 0.473 m$^2$/g.

In the foregoing examples, urea in the form of prills is feed from a hopper into the air mill chamber at a predetermined flow rate. Inside the mill, the prills of urea are subjected to blasts of air from multiple angles. The force of the air blasts causes the prills to impact one another forcefully, so that the prills shatter. The self-impact process is controlled via the introduction of the air blasts into the chamber of the air mill using a precisely controlled source of high air pressure, such that the degree of size reduction of urea particles by impact with one another is consequently very controlled. The desired size reduction is achieved by controlling a combination of pressure and duration of the process. Once a desired level of size reduction of the urea particles is achieved, the urea is removed from the air mill and packaged.

Although the present invention has been described with reference to certain embodiments, other embodiments may achieve similar results and advantages. Variations and modifications of the present invention will be apparent to one skilled in the art and the above disclosure is intended to cover all such modifications and equivalents.

What is claimed is:

1. A process of producing urea preparations having a mean particle-size less than 50 $\mu$m and a purity of about 97% or greater using an air milling process.

2. A process of claim 1, wherein the mean particle-size is less than 40 $\mu$m.

3. A process of claim 1, wherein the mean particle-size is less than 20 $\mu$m.

4. A process of claim 1, the mean particle-size is about 15 $\mu$m.

5. A process of claim 1, wherein the urea preparation has a particle-size distribution with a standard deviation of less than 1.7.

6. A process of claim 1, wherein the urea preparation has a particle-size distribution with a standard deviation from about 1.55 to about 1.65.

7. A process of claim 1, wherein the urea preparation has a particle-size distribution with a standard deviation less than 1.65.

8. A process of claim 1, wherein the urea preparation has a particle-size distribution with a standard deviation of about 1.55.

9. A process of claim 1, wherein the urea preparation has a purity of about 98.5%.

10. A preparation of urea having a mean particle-size of less than about 50 μm and a purity of about 97% or greater.

11. A preparation of urea of claim 10, wherein the mean particle size is less than about 40 μm.

12. A preparation of urea of claim 10, wherein the mean particle-size is less than about 20 μm.

13. A preparation of urea of claim 10, wherein the mean particle-size is about 15 μm.

14. A preparation of urea of claim 10, wherein the urea preparation has a particle-size distribution with a standard deviation of about 1.55 to about 1.65.

15. A preparation of urea of claim 10, wherein the urea preparation has a particle-size distribution with a standard deviation of less than 1.65.

16. A preparation of urea of claim 10, wherein the urea preparation has a particle-size distribution with a standard deviation of about 1.55.

17. An urea preparation having a particle-size of less than about 75 μm, a mean particle-size of less than about 40 μm, a particle-size distribution having a standard deviation of less than about 1.7, and a purity of greater than about 98.5%.

18. A process for producing a rubber compound comprising adding a preparation of urea having a mean particle-size of less than about 50 μm and a purity of about 97% or greater during curing of the rubber compound.

19. A process according to claim 18, further comprising the addition of a blowing agent.

20. A process according to claim 19, wherein the blowing agent is an azodicarbonamide agent.

21. A process according to claim 18, further comprising the addition of an accelerator.

22. A process according to claim 21, wherein the accelerator is selected from the group consisting of thiazole, thiuram, and dithiocarbamate.

23. A process according to claim 18, wherein the addition of the urea preparation reduces coloring of the rubber compound.

24. A process according to claim 18, wherein the addition of the urea compound reduces odor of the rubber compound.

25. A rubber compound comprising rubber and a preparation of urea having a mean particle-size of less than about 50 μm and a purity of about 97% or greater.

* * * * *